(12) United States Patent
Doerner et al.

(10) Patent No.: US 6,696,623 B1
(45) Date of Patent: *Feb. 24, 2004

(54) METHOD OF INCREASING GROWTH AND YIELD IN PLANTS

(75) Inventors: Peter W. Doerner, San Diego, CA (US); Christopher J. Lamb, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/684,169

(22) Filed: Oct. 5, 2000

Related U.S. Application Data

(63) Continuation of application No. 08/683,242, filed on Jul. 18, 1996.

(51) Int. Cl.$^7$ .......................... C12N 15/82; A01H 5/00; A01H 5/10
(52) U.S. Cl. ....................................... 800/298; 800/290
(58) Field of Search ................................ 800/298, 290; 435/468, 419

(56) References Cited

U.S. PATENT DOCUMENTS

| | | | | |
|---|---|---|---|---|
| 5,750,862 A | | 5/1998 | John ........................... | 800/205 |
| 6,087,175 A | * | 7/2000 | John ........................... | 43/419 |

OTHER PUBLICATIONS

Riou–Khamlichi, et al "Cytokinin Activation of Arabidopsis Cell Division Through a D–Type Cyclin", Mar. 1999, Science vol. 283 pp. 1541–1544.*
Cockcroft, et al, "Cyclin D control of growth rate in plants", Jun. 2000, Nature vol. 405 pp. 575–579.*
Doerner et al. (1996) Control of root growth and development of cyclin expression. Nature. 380:520–523.
Courtesy copy of European Patent Office communication dated Nov. 23, 2001 and a courtesy copy of the Supplementary European Search Report.
Doonan, John, Plant Growth: Roots in the Cell Cycle, *Current Biology, vol. 6 No. 7:788–789 (1996)*.
Den Boer, Bart GW and Murray, James AH, Control of Plant Growth and Development Through Manipulation of Cell–Cycle Genes, *Current Opinion in Biotechnology 11:138–145 (2000)*.
Renaudin, Jean Pierre, et al., Plant Cyclins: A Unified Nomenclature For Plant A–, B–, and D–Type Cyclins Based On Sequence Organization, *Plant Molecular Biology 32:1003–1018 (1996)*.
Chandler et al. (1989) Two regulatory genes of hte maize anthocyanin pathway are homologous: Isolation of B utilizing R genomic sequences. The Plant Cell. 1:1175–1183.
Doerner (1994) Cell cycle regulation in plants. Plant Physiol. 106:823–827.

Dooner et al. (1991) Genetic and developmental control of anthocyanin bosynethesis. Annu, Rev. Genet. 25:173–99.
Ferreira et al. (1994) Control of cell proliferation during plant development. Plant Molecule Biology. 26:1289–1303.
Hata et al. (1991) Isolation and characterization of cDNA clones for plant cyclins. The EMBO Journal. 10:9:2681–2688.
Hemerly et al. (1992) Genes regulating the plant cell cycle: Isolation of a mitotic–like cyclin from *Arabidopsis thaliana*. Proc. Nat. Acad. Sci. USA. 89:3295–3299.
Hemerly et al. (1995) Dominant negative mutants of the Cdc2 kinase uncouple cell division from iterative plant development. The EMBO Journal. 14 (15):3925–3936.
Holton et al. (1995) Genetics and biochemistry of anthocyanin biosynthesis. The Plant Cell. 7:1071–1083.
Hrabak et al. (1996) Characterization of eight new members of hte calmodulin–like domain protein kinase gene family from *Arabidopsis thaliana*. Plant Molecular Biology. 31:405–412.
Koff et al. (1991) Human cyclin E, a new cyclin that interacts with two members of the CDC2 gene family. Cell. 66:1217–1228.
Leopold et al. (1991) An evolutionary conserved cyclin homolog from drosophila rescues yeast deficient in G1 cyclins. Cell. 66:1207–1216.
Lew et al. (1991) Isolation of three novel human cyclins by rescue of G1 cyclin (cin) function in yeast. Cell. 66:1197–1206.
Lloyd AM et al. (1992) Arabidopsis and nicotiana anthocyanin production activated by maize regulators R and C1. Science. 258:1773–1775.
Napoli et al. (1990) Introduction of a chimeric chalcone synthase gene into petunia results in reversible co–suppression of homologous genes in trans. The Plant Cell. 2:279–289.
Renaudin et al. (1996) Plant cyclins: a unified nomenclature for plant A–,B–, and D–type cyclins based on sequence organization. Plant Molecular Biology. 32:1003–1018.
Schwob et al. (1993) CLB5 and CLB6, a new pair of B cyclin involved in DNA replication, Saccharomyces Cerevisiae, Genes and Development. 7:1160–1175.

* cited by examiner

*Primary Examiner*—Elizabeth F. McElwain
*Assistant Examiner*—Cynthia Collins
(74) *Attorney, Agent, or Firm*—Knobbe, Martens, Olson & Bear, LLP

(57) ABSTRACT

The invention provides a method of producing a genetically modified plant characterized as having increased growth and yield as compared to a corresponding wild-type plant comprising increasing the level of cyclin expression in the plant. Genetically modified plants characterized as having increased growth and yield are also provided.

9 Claims, 4 Drawing Sheets

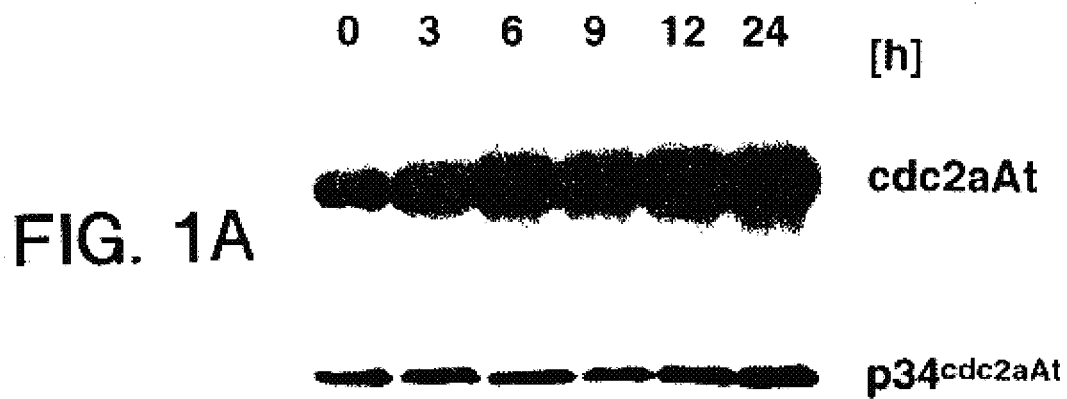
FIG. 1A
FIG. 1B
FIG. 1C

METHOD OF INCREASING GROWTH AND YIELD IN PLANTS

RELATED APPLICATIONS

This application is a continuation application of U.S. patent application 08/683,242, filed Jul. 18, 1996, which is hereby incorporated by reference.

FIELD OF THE INVENTION

The present invention relates generally to plant genetic engineering, and specifically to a method for producing genetically engineered plants characterized as having increased growth and yield.

BACKGROUND OF THE INVENTION

For each plant species, there exists a wide discrepancy in plant growth due to environmental conditions. Under most conditions, the maximum growth potential of a plant is not realized. Plant breeding has demonstrated that a plant's resources can be redirected to individual organs to enhance growth.

Genetic engineering of plants, which entails the isolation and manipulation of genetic material, e.g., DNA or RNA, and the subsequent introduction of that material into a plant or plant cells, has changed plant breeding and agriculture considerably over recent years. Increased crop food values, higher yields, feed value, reduced production costs, pest resistance, stress tolerance, drought resistance, the production of pharmaceuticals, chemicals and biological molecules as well as other beneficial traits are all potentially achievable through genetic engineering techniques.

The ability to manipulate gene expression provides a means of producing new characteristics in transformed plants. For example, the ability to increase the size of a plant's root system would permit increased nutrient assimilation from the soil. Moreover, the ability to increase leaf growth would increase the capacity of a plant to assimilate solar energy. Obviously, the ability to control the growth of an entire plant, or specific target organs thereof would be very desirable.

SUMMARY OF THE INVENTION

The present invention is based on the discovery that increased growth and yield in plants can be achieved by elevating the level of cyclin expression.

In a first embodiment, the invention provides a method of producing a genetically modified plant characterized as having increased growth and yield as compared to a corresponding wild-type plant. The method comprises contacting plant cells with nucleic acid encoding a cyclin protein, wherein the nucleic acid is operably associated with a regulatory sequence, to obtain transformed plant cells; producing plants from the transformed plant cells; and selecting a plant exhibiting said increased yield. The cyclin-encoding nucleic acid preferably encodes the cyclin cyc1aAt.

In another embodiment, the invention provides a method of producing a plant characterized as having increased yield, the method comprising contacting a plant with an agent which elevates cyclin expression above cyclin expression in a plant not contacted with the agent. The agent may be a transcription factor or a chemical agent which induces an endogenous cyclin promoter or other chemically inducible promoter driving expression as the cyclin transgene.

The invention also provides plants, plant tissue and seeds produced by the methods of the invention.

BRIEF DESCRIPTION OF THE DRAWING

FIG. 1 shows steady state levels of cdc2aAt mRNA and p34 protein, panel a; cyc1aAt mRNA during IAA induction of lateral root meristems, panel b; cyc1aAt mRNA in selected non-induced transgenic lines, panel c; normalized transcript levels relative to wild-type are indicated. Col-0, wild-type; 1A2, 2A5, 4A3, 11A1: T2 homozygous; 6A, 7A, 8A: T1 heterozygous transgenic lines.

DESCRIPTION OF THE PREFERRED EMBODIMENTS

Figure 2A:
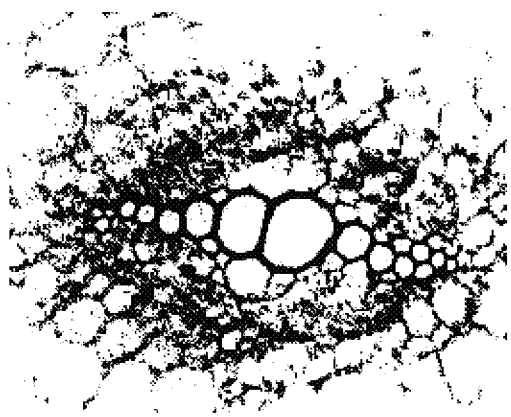
FIG. 2 shows an in situ hybridization analysis of cdc2aAt and cyc1aAt transcripts in root apices and developing lateral roots. Panels a–d show cross sections of quiescent roots (panels a,b) or proliferating cells in primordia (panels c,d) that were hybridized to cdc2aAt (a) or cyc1aAt (b–d) anti-sense probes. Panels e, f show cyc1aAt mRNA abundance in contiguous meristematic cell files in root apices. Transcript accumulation is indicated by silver grain deposition and visualized by indirect red illumination. Scale bar is 10 $\mu$m in a–d, 5 $\mu$m in e. fc, founder cell accumulating cyc1aAt transcripts; p, pericycle cell layer; r, towards the root apex; s, towards the shoot.
Figure 2B:
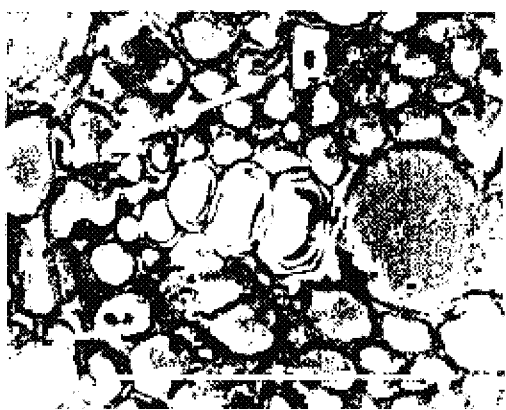
Figure 2C:
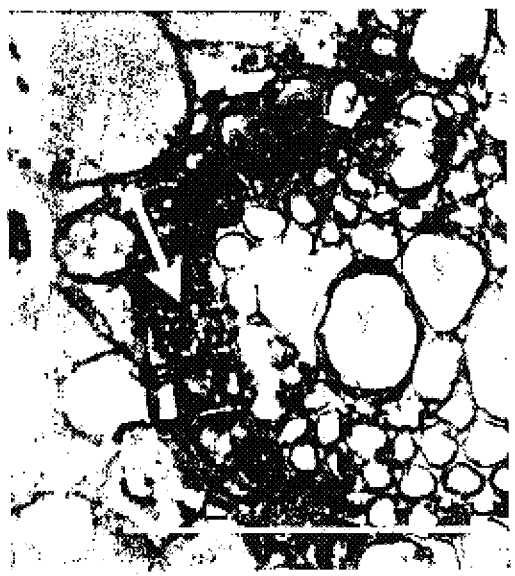
Figure 2D:
Figure 2E:
Figure 2F:
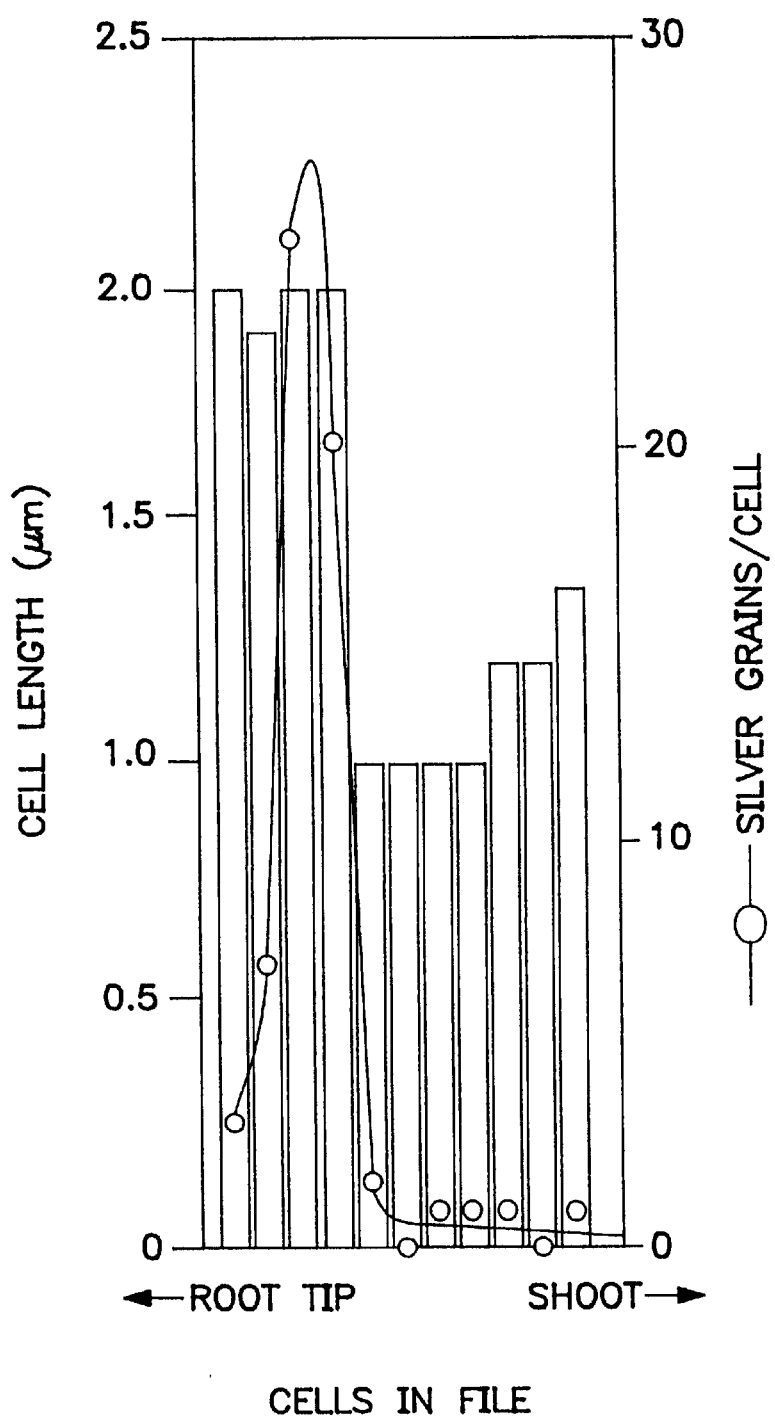

The present invention provides methods for increasing the yield of a plant, such as a agricultural crop, by elevating the cyclin expression level in the plant. Increased cyclin expression in plant cells competent to divide results in increased plant growth.

In a preferred embodiment, the invention provides a method for producing a genetically modified plant characterized as having increased yield as compared to a plant which has not been genetically modified (e.g., a wild-type plant). The method comprises contacting plant cells with nucleic acid encoding a cyclin protein, wherein the nucleic acid is operably associated with a regulatory sequence to obtain transformed plant cells; producing plants from the transformed plant cells; and thereafter selecting a plant exhibiting increased growth and yield.

As used herein, the term "yield" or "plant yield" refers to increased crop growth, and/or increased biomass. In one embodiment, increased yield results from increased growth rate and increased root size. In another embodiment, increased yield is derived from shoot is growth. In still another embodiment, increased yield is derived from fruit growth.

The term "genetic modification" as used herein refers to the introduction of one or more exogenous nucleic acid sequences, e.g., cyclin encoding sequences, as well as regulatory sequences, into one or more plant cells, which can generate whole, sexually competent, viable plants. The term "genetically modified" as used herein refers to a plant which has been generated through the aforementioned process. Genetically modified plants of the invention are capable of self-pollinating or cross-pollinating with other plants of the same species so that the foreign gene, carried in the germ line, can be inserted into or bred into agriculturally useful plant varieties. The term "plant cell" as used herein refers to protoplasts, gamete producing cells, and cells which regenerate into whole plants.

As used herein, the term "plant" refers to either a whole plant, a plant part, a plant cell, or a group of plant cells, such as plant tissue or plant seed. Plantlets are also included within the meaning of "plant". Plants included in the invention are any plants amenable to transformation techniques, including gymnosperms and angiosperms, both monocotyledons and dicotyledons.

Examples of monocotyledonous angiosperms include, but are not limited to, asparagus, field and sweet corn, barley, wheat, rice, sorghum, onion, pearl millet, rye and oats and other cereal grains. Examples of dicotyledonous angiosperms include, but are not limited to tomato, tobacco, cotton, rapeseed, field beans, soybeans, peppers, lettuce, peas, alfalfa, clover, cole crops or *Brassica oleracea* (e.g., cabbage, broccoli, cauliflower, brussel sprouts), radish, carrot, beets, eggplant, spinach, cucumber, squash, melons, cantaloupe, sunflowers and various ornamentals. Examples of woody species include poplar, pine, sequoia, cedar, oak, etc.

The term "exogeneous nucleic acid sequence" as used herein refers to a nucleic acid foreign to the recipient plant host or, native to the host if the native nucleic acid is substantially modified from its original form. For example, the term includes a nucleic acid originating in the host species, where such sequence is operably linked to a promoter that differs from the natural or wild-type promoter. In the broad method of the invention, at least one nucleic acid sequence encoding cyclin is operably linked with a promoter. It may be desirable to introduce more than one copy of cyclin polynucleotide into a plant for enhanced cyclin expression. For example, multiple copies of a cyclin polynucleotide would have the effect of increasing production of cyclin even further in the plant.

The term "regulatory sequence" as used herein refers to a nucleic acid sequence capable of controlling the transcription of an operably associated gene. Therefore, placing a gene under the regulatory control of a promoter or a regulatory element means positioning the gene such that the expression of the gene is controlled by the regulatory sequence(s). In general, promoters are found positioned 5' (upstream) of the genes that they control. Thus, in the construction of promoter gene combinations, the promoter is preferably positioned upstream of the gene and at a distance from the transcription start site that approximates the distance between the promoter and the gene it controls in the natural setting. As is known in the art, some variation in this distance can be tolerated without loss of promoter function. Similarly, the preferred positioning of a regulatory element, such as an enhancer, with respect to a heterologous gene placed under its control reflects its natural position relative to the structural gene it naturally regulates.

Cyclin-encoding nucleic acids utilized in the present invention include nucleic acids encoding mitotic cyclins such as, for example, cyclin B; nucleic acids encoding S-phase cyclins such as, for example cyclin A, and nucleic acids encoding G1 phase cyclins. Specific cyclins which can be utilized herein include cyc1aAt, cyc3aAt, cyc3bAt, cycd1, cycd2 and the like. Preferably, the nucleic acid used in the method of the invention encodes the cyc1aAt protein (Genebank Accession No. X62279).

Genetically modified plants of the present invention are produced by contacting a plant cell with a nucleic acid sequence encoding the desired cyclin. To be effective once introduced into plant cells, the cyclin-encoding nucleic acid must be operably associated with a promoter which is effective in plant cells to cause transcription of the cyclin transgene. Additionally, a polyadenylation sequence or transcription control sequence, also recognized in plant cells, may also be employed. It is preferred that the nucleic acid be introduced via a vector and that the vector harboring the nucleic acid sequence also contain one or more selectable marker genes so that the transformed cells can be selected from non-transformed cells in culture, as described herein.

The term "operably associated" refers to functional linkage between a regulatory sequence, preferably a promoter sequence, and the cyclin-encoding nucleic acid sequence regulated by the promoter. The operably linked promoter controls the expression of the cyclin nucleic acid sequence.

The expression of cyclin genes employed in the present invention may be driven by a number of promoters. Although the endogenous, or native promoter of a structural gene of interest may be utilized for transcriptional regulation of the gene, preferably, the promoter is a foreign regulatory sequence.

When it is desired to increase growth and yield in the whole plant, cyclin expression should be directed to all cells in the plant which are capable of dividing. This can be accomplished by using a promoter active in all meristems. Such promoters include, for example, the cdc2a promoter and the cyc07 promoter. (See for example, Ito et al., *Plant Mol. Biol.*, 24:863, 1994; Martinez et al., *Proc. Natl. Acad. Sci. USA*, 89:7360, 1992; Medford et al., *Plant Cell*, 3:359, 1991; Terada et al., *Plant Journal*, 3:241, 1993; Wissenbach et al., *Plant Journal*, 4:411, 1993).

When it is desired to increase growth and yield in a specific organ, cyclin expression should be targeted to the appropriate meristem, e.g., the shoot meristem, the floral meristem, the root meristem etc. This can be accomplished by using a tissue specific promoter. Examples of tissue specific promoters active in shoot meristems are described in Atanassova et al., *Plant Journal*, 2:291, 1992 and Medford et al., *Plant Cell*, 3:359, 1991. Examples of tissue specific promoters active in floral meristems are the promoters of the agamous and apetala 1 genes are described in Bowman et al., *Plant Cell*, 3:749, 1991; and Mandel et al., *Nature*, 360:273, 1992.

The particular promoter selected should be capable of causing sufficient cyclin expression to cause increased yield and/or increased biomass. It should be understood that cyclin expression can be altered in cells that are competent to divide. The promoters used in the vector constructs of the present invention may be modified, if desired, to affect their control characteristics.

Optionally, a selectable marker may be associated with the cyclin-encoding nucleic acid. As used herein, the term "marker" refers to a gene encoding a trait or a phenotype which permits the selection of, or the screening for, a plant or plant cell containing the marker. Preferably, the marker gene is an antibiotic resistance gene whereby the appropriate antibiotic can be used to select for transformed cells from among cells that are not transformed. Examples of suitable selectable markers include adenosine deaminase, dihydrofolate reductase, hygromycin-B-phosphotransferase, thymidine kinase, xanthine-guanine phospho-ribosyltransferase and amino-glycoside 3'-O-phosphotransferase II. Other suitable markers will be known to those of skill in the art.

To commence a transformation process in accordance with the present invention, it is first necessary to construct a suitable vector and properly introduce it into the plant cell. Vector(s) employed in the present invention for transformation of a plant cell include a cyclin-encoding nucleic acid sequence operably associated with a promoter. Details of the construction of vectors utilized herein are known to those skilled in the art of plant genetic engineering.

Cyclin-encoding nucleic acid sequences utilized in the present invention can be introduced into plant cells using Ti plasmids of *Agrobacterium tumefaciens* (*A. tumefaciens*), root-inducing (Ri) plasmids of *Agrobacterium rhizogenes* (*A. rhizogenes*), and plant virus vectors. (For reviews of such techniques see, for example, Weissbach & Weissbach, 1988, Methods for Plant Molecular Biology, Academic Press, N.Y., Section VIII, pp. 421–463; and Grierson & Corey, 1988, Plant Molecular Biology, 2d Ed., Blackie, London, Ch. 7–9, and Horsch et al, *Science*, 227:1229, 1985, both incorporated herein by reference). In addition to plant transformation vectors derived from the Ti or Ri plasmids of Agrobacterium, alternative methods may involve, for example, the use of liposomes, electroporation, chemicals that increase free DNA uptake, transformation using viruses or pollen and the use of microprojection.

One of skill in the art will be able to select an appropriate vector for introducing the cyclin-encoding nucleic acid sequence in a relatively intact state. Thus, any vector which will produce a plant carrying the introduced cyclin-encoding nucleic acid should be sufficient. Even use of a naked piece of DNA would be expected to confer the properties of this invention, though at low efficiency. The selection of the vector, or whether to use a vector, is typically guided by the method of transformation selected.

The transformation of plants in accordance with the invention may be carried out in essentially any of the various ways known to those skilled in the art of plant molecular biology. (See, for example, Methods of Enzymology, Vol. 153, 1987, Wu and Grossman, Eds., Academic Press, incorporated herein by reference). As used herein, the term "transformation" means alteration of the genotype of a host plant by the introduction of cyclin-nucleic acid sequence.

For example, a cyclin-encoding nucleic acid can be introduced into a plant cell utilizing *A. tumefaciens* containing the Ti plasmid, as mentioned briefly above. In using an *A. tumefaciens* culture as a transformation vehicle, it is most advantageous to use a non-oncogenic strain of Agrobacterium as the vector carrier so that normal non-oncogenic differentiation of the transformed tissues is possible. It is also preferred that the Agrobacterium harbor a binary Ti plasmid system. Such a binary system comprises 1) a first Ti plasmid having a virulence region essential for the introduction of transfer DNA (T-DNA) into plants, and 2) a chimeric plasmid. The chimeric plasmid contains at least one border region of the T-DNA region of a wild-type Ti plasmid flanking the nucleic acid to be transferred. Binary Ti plasmid systems have been shown effective in the transformation of plant cells (De Framond, *Biotechnology*, 1:262, 1983; Hoekema et al., Nature, 303:179, 1983). Such a binary system is preferred because it does not require integration into the Ti plasmid of *A. tumefaciens*, which is an older methodology.

Methods involving the use of Agrobacterium in transformation according to the present invention include, but are not limited to: 1) co-cultivation of Agrobacterium with cultured isolated protoplasts; 2) transformation of plant cells or tissues with Agrobacterium; or 3) transformation of seeds, apices or meristems with Agrobacterium.

In addition, gene transfer can be accomplished by in planta transformation by Agrobacterium, as described by Bechtold et al., (*C.R. Acad Sci. Paris*, 316:1194, 1993) and exemplified in the Examples herein. This approach is based on the vacuum infiltration of a suspension of Agrobacterium cells.

The preferred method of introducing a cyclin-encoding nucleic acid into plant cells is to infect such plant cells, an explant, a meristem or a seed, with transformed *A. tumefaciens* as described above. Under appropriate conditions known in the art, the transformed plant cells are grown to form shoots, roots, and develop further into plants.

Alternatively, cyclin-encoding nucleic acid can be introduced into a plant cell using mechanical or chemical means. For example, the nucleic acid can be mechanically transferred into the plant cell by microinjection using a micropipette. Alternatively, the nucleic acid may be transferred into the plant cell by using polyethylene glycol which forms a precipitation complex with genetic material that is taken up by the cell.

Cyclin-encoding nucleic acid can also be introduced into plant cells by electroporation (Fromm et al., *Proc. Natl. Acad. Sci., USA.*, 82:5824, 1985, which is incorporated herein by reference). In this technique, plant protoplasts are electroporated in the presence of vectors or nucleic acids containing the relevant nucleic acid sequences. Electrical impulses of high field strength reversibly permeabilize membranes allowing the introduction of nucleic acids. Electroporated plant protoplasts reform the cell wall, divide and form a plant callus. Selection of the transformed plant cells with the transformed gene can be accomplished using phenotypic markers as described herein.

Another method for introducing a cyclin-encoding nucleic acid into a plant cell is high velocity ballistic penetration by small particles with the nucleic acid to be introduced contained either within the matrix of such particles, or on the surface thereof (Klein et al., *Nature* 327:70, 1987). Bombardment transformation methods are also described in Sanford et al. (*Techniques* 3:3–16, 1991) and Klein et al. (*Bio/Techniques* 10:286, 1992). Although, typically only a single introduction of a new nucleic acid sequence is required, this method particularly provides for multiple introductions.

Cauliflower mosaic virus (CaMV) may also be used as a vector for introducing nucleic acid into plant cells (U.S. Pat. No. 4,407,956). CaMV viral DNA genome is inserted into a parent bacterial plasmid creating a recombinant DNA molecule which can be propagated in bacteria. After cloning, the recombinant plasmid again may be cloned and further modified by introduction of the desired nucleic acid sequence. The modified viral portion of the recombinant plasmid is then excised from the parent bacterial plasmid, and used to inoculate the plant cells or plants.

As used herein, the term "contacting" refers to any means of introducing a cyclin-encoding nucleic acid into a plant cell, including chemical and physical means as described above. Preferably, contacting refers to introducing the nucleic acid or vector containing the nucleic acid into plant cells (including an explant, a meristem or a seed), via *A. tumefaciens* transformed with the cyclin-encoding nucleic acid as described above.

Normally, a plant cell is regenerated to obtain a whole plant from the transformation process. The immediate product of the transformation is referred to as a "transgenote". The term "growing" or "regeneration" as used herein means growing a whole plant from a plant cell, a group of plant cells, a plant part (including seeds), or a plant piece (e.g., from a protoplast, callus, or tissue part).

Regeneration from protoplasts varies from species to species of plants, but generally a suspension of protoplasts is first made. In certain species, embryo formation can then be induced from the protoplast suspension. The culture media will generally contain various amino acids and hormones, necessary for growth and regeneration. Examples of hormones utilized include auxins and cytokinins. Efficient regeneration will depend on the medium, on the genotype, and on the history of the culture. If these variables are controlled, regeneration is reproducible.

Regeneration also occurs from plant callus, explants, organs or parts. Transformation can be performed in the context of organ or plant part regeneration. (see *Methods in Enzymology*, Vol. 118 and Klee et al., *Annual Review of Plant Physiology*, 38:467, 1987). Utilizing the leaf disk-transforrnation-regeneration method of Horsch et al., *Science*, 227:1229, 1985, disks are cultured on selective media, followed by shoot formation in about 2–4 weeks. Shoots that develop are excised from calli and transplanted to appropriate root-inducing selective medium. Rooted plantlets are transplanted to soil as soon as possible after roots appear. The plantlets can be repotted as required, until reaching maturity.

In vegetatively propagated crops, the mature transgenic plants are propagated by utilizing cuttings or tissue culture techniques to produce multiple identical plants. Selection of desirable transgenotes is made and new varieties are obtained and propagated vegetatively for commercial use.

In seed propagated crops, mature transgenic plants can be self crossed to produce a homozygous inbred plant. The resulting inbred plant produces seed containing the newly introduced foreign gene(s). These seeds can be grown to produce plants that would produce the selected phenotype, e.g. increased yield.

Parts obtained from regenerated plant, such as flowers, seeds, leaves, branches, roots, fruit, and the like are included in the invention, provided that these parts comprise plant cells that have been transformed as described. Progeny and variants, and mutants of the regenerated plants are also included within the scope of the invention, provided that these parts comprise the introduced nucleic acid sequences.

Plants exhibiting increased growth and/or yield as compared with wild-type plants can be selected by visual observation. The invention includes plants produced by the method of the invention, as well as plant tissue and seeds.

In another embodiment, the invention provides a method of producing a plant characterized as having increased growth and yield by contacting a plant capable of increased yield with a cyclin promoter-inducing amount of an agent which induces cyclin gene expression. Induction of cyclin gene expression results in production of a plant having increased yield as compared to a plant not contacted with the agent.

A "plant capable of increased yield" refers to a plant that can be induced to express its endogenous cyclin gene to achieve increased yield. The term "promoter inducing amount" refers to that amount of an agent necessary to elevate cyclin gene expression above cyclin expression in a plant cell not contacted with the agent, by stimulating the endogenous cyclin promoter. For example, a transcription factor or a chemical agent may be used to elevate gene expression from native cyclin promoter, thus inducing the promoter and cyclin gene expression.

The invention also provides a method of providing increased transcription of a nucleic acid sequence in a selected tissue. The method comprises growing a plant having integrated in its genome a nucleic acid construct comprising, an exogenous gene encoding a cyclin protein, said gene operably associated with a tissue specific whereby transcription of said gene is increased in said selected tissue.

Plant development is plastic with post-embryonic organogenesis mediated by meristems (Steeves and Sussex, *Patterns in Plant Development*, 1–388 (Press Syndicate of the University of Cambridge, Cambridge, 1989)). Although cell division is intrinsic to meristem initiation, maintenance and proliferative growth, the role of the cell cycle in regulating growth and development is unclear. To address this question, the expression of cdc2 and cyclin genes, which encode the catalytic and regulatory subunits, respectively, of cyclin-dependent protein kinases controlling cell cycle progression (Murray and Hunt, *The Cell Cycle* (New York), 1993) were examined. Unlike cdc2, which is expressed not only in apical meristems but also in quiescent meristems, (Martinez et al., *Proc. Natl. Acad Sci. USA*, 89:7360, 1992), transcripts of cyc1aAt accumulated specifically in active meristems and dividing cells immediately before cytokinesis. Ectopic expression of cyc1aAt under control of the cdc2aAt promoter in Arabidopsis plants markedly accelerated growth without altering the pattern of development or inducing neoplasia. Thus, cyclin expression is a limiting factor for growth.

The above disclosure generally describes the present invention. A more complete understanding can be obtained by reference to the following specific examples which are provided herein for purposes of illustration only and are not intended to limit the scope of the invention.

EXAMPLE 1

A full length cyc1aAt cyclin cDNA was placed under control of the Arabidopsis cdc2aAt promoter (Hemerly et al., 1992, supra). The chimeric gene was cloned into a T-DNA transformation vector carrying the selection marker hygromycin phospho-transferase (Hyg') and transformed into Arabidopsis using the vacuun-infiltration method (Bechtold and Pelletier, *Acad. Sci. Paris, Life Sci.*, 316:1194, 1993) to introduce *Agrobacterium tumefaciens*. Several independent transgenic lines having elevated steady-state levels of cyc1aAt mRNA showed a dramatic increase of both main and lateral root growth rate, correlated with proportionally increased fresh weight, dry mass and DNA content, but not cell size. Enhanced growth was orderly, with no observed differences in morphology and clearly not neoplastic.

Arabidopsis seedlings (ecotype Columbia) were grown in 20 ml MS medium (Murashige and Skoog, *Physiol. Plant.*, 15:473, 1962). Eight- to 10-day-old plants were transferred to MS medium buffered with 50 mM potassium phosphate, pH 5.5, and initiation of lateral roots was stimulated by addition of IAA to 10 $\mu M_{eff}$ (non-dissociated IAA). Roots were collected at the time points indicated and total RNA and protein isolated. 500 ng poly(A)+ RNA was separated on 1% formaldehyde gels (Ausubel et al, *Current Protocols in Molecular Biology*, Green Publishing Associates and Wiley-Interscience, New York, 1987), transferred to Nytran membranes (Schleicher and Schuill) and hybridized to $^{32}$P-labeled probes corresponding to nucleotides (nt) 674–1004 of cyc1aAt (Hemerly et al., *Proc. Natl. Acad. Sci. USA*, 89:3295, 1992), or nt 661–1386 of Arabidopsis cdc2aAt (Hirayama et al., Gene, 105:159, 1991), followed by hybridization with nt 2576–2824 of Arabidopsis UBQ3 (Norris et al., *Plant Mol. Biol.*, 21:895, 1993) for normalization. Blots were quantified with a Molecular Dynamics Phosphorimager. cyc1aAt is a single copy gene in Arabidopsis. Total protein was separated on 12% SDS-PAGE and transferred to PVDF membranes. p34$^{cdc2aAt}$ was detected with serum raised in rabbits against the peptide YFKDLGGMP (SEQ ID NO:1), corresponding to amino acids 286–294, and visualized by Enhanced Chemiluminescence Assay (Amersham).

FIG. 1 shows steady state levels of cdc2aAt mRNA and p34 protein, panel a; cyc1aAt mRNA during IAA induction of lateral root meristems, panel b; cyc1aAt mRNA in selected non-induced transgenic lines, panel c; normalized transcript levels relative to wild-type are indicated. Col-0, wild-type; 1A2, 2A5, 4A3, 11A1: T2 homozygous; 6A, 7A, 8A: T1 heterozygous transgenic lines. cyc1aAt mRNA levels in the lines 4A3, 6A, 7A, 8A, and 3A exceeded those of IAA induced wild-type roots.

The levels of cdc2 mRNA and p34$^{cdc2}$ protein per cell did not markedly change following stimulation of lateral root initiation by the auxin indoleacetic acid (IAA) (FIG. 1, panel a). Hence, while cdc2 expression is correlated with the competence to divide, root growth and initiation of lateral roots do not appear to be limited by the abundance of the cyclin-dependent protein kinase p34 catalytic subunit and, moreover, ectopic expression of cdc2 in transgenic Arabidopsis failed to perturb growth or development (Hemerly et al., *EMBO J.*, 14:3925, 1995).

In contrast, IAA treatment of Arabidopsis roots induced the expression of several cyc genes from low basal levels and in particular cyc1aAt mRNA, which encodes a mitotic cyclin (Hemerly et al., supra)), exhibited a rapid 15 to 20-fold increase (FIG. 1, panel b).

FIG. 2 shows an in situ hybridization analysis of cdc2aAt and cyc1aAt transcripts in root apices and developing lateral roots. Panels a–d show cross sections of quiescent roots (panels a,b) or proliferating cells in primordia (panels c,d) that were hybridized to cdc2aAt (a) or cyc1aAt (b–c) antisense probes. Panels e,f show cyc1aAt mRNA abundance in contiguous meristematic cell files in root apices. Transcript accumulation is indicated by silver grain deposition and visualized by indirect red illumination. Scale bar is 10 μm in a–d, 5 μm in e. fc, founder cell accumulating cyc1aAt transcripts; p, pericycle cell layer; r, towards the root apex; s, towards the shoot.

Tissue samples were processed for in situ hybridization to examine expression of cyclin transcripts. The samples were treated with 10 μM IAA. After 8 or 24 h incubation, radish (*Raphanus sativa* var Scarlet Globe) roots were processed as described (Drews et al., Cell, 65:991, 1991). Sections (8 μm) were hybridized to a $^{33}$P-labeled RNA probe, corresponding to nt 674–1004 of cycla1aAt (Hemerly et aL, supra) (FIG. 2, panels b–e) or to a $^{35}$S-labeled probe used in a corresponding to nt 661–1386 of cdc2aAt (Hirayama et al., supra), for 14 h at 48° C. in 50% formamide. After hybridization, the final washes were for 1 h at 58° C. in 0.015 m NaCl and slides were then exposed for 3 weeks (cyc1aAt) or 5d (cdc2aAt). After developing, silver grains were illuminated laterally with red light, specimens were visualized by phase contrast and double exposures were taken on FUJI Velvia film. Images were assembled in ADOBE Photoshop. For the analysis summarized in FIG. 2, panel f silver grains were counted and cell size measured in the cell file shown in FIG. 2, panel e.

In situ hybridization showed that, unlike cdc2, cyc1aAt transcripts were not detected in quiescent pericycle cells, but accumulated in single, cytoplasmically dense cells of incipient lateral root primordia, and in the emergent organ cyc1aAt was expressed exclusively in the meristem (FIG. 2, panels a–d). Moreover, crucifer roots consisted of long cell files that arise by transverse divisions followed by longitudinal expansion (Dolan el al., *Development*, 119:71, 1993), and within such a contiguous spatial display of sequential cell division phases, cyc1aAt transcripts accumulated only in large cells immediately prior to cytokinesis, declining to background levels in the adjacent small daughter cells (FIG. 2, panels e,f). A similar, stringent spatio-temporal relationship of cyclin expression and mitosis was observed in Antirrhinum shoot apical meristems (Fobert el al., *EMBO J.*, 13:616, 1994).

The close correlation between cyc1aAt expression and cell division during growth of the root apical meristem and the initiation of lateral roots, together with the pattern of cyc1aAt promoter activity deduced from the expression of cyc1aAt::uidA gene fusions in transgenic Arabidopsis (Ferreira et al., *Plant Cell*, 6:1763, 1994), suggested that cyclin abundance might be a key factor regulating root growth and development. To test this hypothesis transgenic Arabidopsis were generated (Bechtold and Pelletier, *Acad Sci. Paris, Life Sci.*, 316:1194, 1993) containing cyc1aAt under control of the cdc2aAt promoter. Five transformants were obtained in which the level of cyc1aAt mRNA in untreated roots exceeded that observed in IAA-stimulated roots of wild-type plants (FIG. 1, panel c), and these lines were chosen for further study.

An NheI site was introduced in the third codon of the cyc1aAt CDNA by in vitro mutagenesis and this open reading frame subsequently ligated to the cdc2aAt promoter with an in vitro generated XbaI site at codon 3. This fragment was ligated into pBiB-Hyg (Becker et al., *Pl. Mol. Biol*, 20:1195, 1992) and transfected into *Agrobacterium tumefaciens* GV3101 (Koncz and Schell, *Mol. Gen. Genet.*, 204:383, 1986). *Arabidopsis thaliana* (*A. thaliana*) (ecotype Columbia) was transformed by vacuum infiltration (Bechtold et al., supra), and transgenic seedlings (T0 generation) were selected on MS plates containing 30 μg/ml hygromycin. 52 independent transgenic lines were obtained and elevated levels of cyc1aAt mRNA were detected in 9 of the 11 lines analyzed in detail. Growth assays were performed on heterozygous T1 and homozygous T2 progeny as indicated.

Figure 3A:
FIG. 3 shows increased root growth rate in *Arabidopsis thaliana* (*A. thaliana*) ectopically expressing cyc1aAt cyclin. Panel a, Wild-type (left) or transgenic line 6A (T1generation) containing the cdc2aAt::cyc1aAt gene fusion (right). Arabidopsis seed were plated on MS (3% sucrose) agar and grown in a vertical orientation for 7 d. Plants transformed with the vector alone or with unrelated promoter::uidA constructs or with a cdc2aAt::cyc1aAt fusion in which the cdc2aAt 5' untranslated leader was interrupted by a DS transposon insertion did not show this phenotype. Panel b, wild-type (left) or transgenic line 6A (T1 generation) (right) 6 d after IAA induction of lateral roots. One week-old seedlings grown hydroponically were treated with 10 $\mu$MIAA$_{eff}$ to stimulate lateral root development.
Figure 3B:

FIG. 3 shows increased root growth rate in Arabidopsis ectopically expressing cyc1aAt cyclin. Panel a, Wild-type (left) or transgenic line 6A (T1 generation) containing the cdc2aAt::cyc1aAt gene fusion (right). Arabidopsis seed were plated on MS (3% sucrose) agar and grown in a vertical orientation for 7 d. Plants transformed with the vector alone or with unrelated promoter::uidA constructs or with a cdc2aAt::cyc1aAt fusion in which the cdc2aAt 5' untranslated leader was interrupted by a DS transposon insertion did not show this phenotype. Panel b, wild-type (left) or transgenic line 6A (T1 generation) (right) 6 d after IAA induction of lateral roots. One week-old seedlings grown hydroponically were treated with 10 μMIAA$_{eff}$ to stimulate lateral root development.

Strong expression of the cdc2aAt::cyc1aAt transgene caused a marked increase in the rate of organized root growth (FIG. 3, panel a). Homozygous or heterozygous seed were plated on MS agar and plants grown in vertical orientation for 7 days with a 16h day/8 h night schedule at 22° C. Four images of each plate were acquired with a Speedlight Platinum frame grabber (Lighttools Research) at 24 h intervals and root growth analyzed with NIH-Image by measuring the displacement of root apices. Following growth analysis, roots from 10 plants of each class were collected and RNA analyzed. To measure cell sizes, roots were cleared by overnight incubation in saturated chloral hydrate, visualized with Normarski optics, photographed and analyzed with NIH-Image. Statistical analysis (t-test with unpaired variances) was performed with MS Excel. Root growth in IAA-treated plants was assessed 3 and 6 d after induction by determination of fresh weight of roots excised from liquid-grown plants and then dry weight following lyophilization for 24 h. Total DNA was extracted from dried material (Ausubel el al., supra).

In heterozygous T2 progeny, increased growth rate, measured by displacement of the apex of the main root in time-lapse photography, strictly co-segregated with transgene expression and individuals lacking the transgene grew at the same rate as wild-type plants (Table 1). The average size of epidermal, cortical, endodermal and pericycle cells was equivalent or slightly reduced in cdc2aAtl::cyc1aAt transformants compared to wild-type plants (Table 2), and hence increased growth reflects increased cell number rather than cell size. The pattern of spontaneous lateral root initiation and overall root morphology were indistinguishable in wild-type and transgenic plants (FIG. 3, panel a). When treated with 1 μMIAA, which induces well-separated lateral root primordia, the frequency of primordia initiated per unit length of the main roots was not altered (mean of 1.08 initials/mm with a standard deviation of 0.09 in wild-type compared with 1.14+/−0.07 and 1.09+/−0.13 in the two transgenic lines examined). However, growth and development of lateral roots following induction by 10 μMIAA, was markedly accelerated in the cdc2aAt::cyc1aAt transformants, giving rise to a much enlarged root system (FIG. 3, panel b). Enhanced root growth in cdc2aAt::cyc1aAt plants following IAA treatment superficially resembles the alf1 phenotype (Celenza et al., *Genes & Development*, 9:2131, 1995) and these plants have elevated levels of cyc1aAt transcripts but in contrast to cdc2aAt::cyc1aAt transformants, alf1 plants initiate supernumerary lateral roots. The several-fold greater gain of fresh weight in IAA-treated cdc2aAt::cyc1aAt plants compared to equivalent wild-type controls was accompanied by marked increased in DNA content and dry weight (Table 3). Confocal microscopy confirmed that the enhanced growth response to IAA, which was also observed in several lines showing weaker cdc2aAt::cyc1aAt expression, did not reflect transgene stimulation of cell vacuolation or elongation. Thus, ectopic cyclin expression enhances root growth by stimulation of cell division activity in meristems, thereby increasing the rate of cell production without altering meristem organization.

The data above indicate that cdc2aAt::cyc1aAt expression is sufficient to enhance growth from established apical meristems, suggesting that cell cycle activity regulates meristem activity. However, the failure to induce gratuitous organ primordia by ectopic expression of cyc1aAt under control of the cdc2aAt promoter implies additional control points in the generation of a new apical meristem, either through post-translational regulation of cyclin-dependent protein kinase activity or the operation of parallel regulatory pathways. In most animal cells, the commitment to cell division occurs late in GI (Pardee, A.B., *Science*, 246:603, 1989), and cyclin D1 and cyclin E are rate-limiting for G1 progression in cultured cells (Ohtsubo and Roberts, *Science*, 259:1908, 1993; Quelle el al., *Genes Dev.*, 7:1559, 1993; Resnitzky and Reed, *Mol. Cell Biol.*, 15:3463, 1995). Elevated levels of cyclin D1 are observed in several tumors (Motokura et al., *Nature*, 350:512, 1991; Rosenberg et al., *Proc. Natl. Acad. Sci. USA*, 88:9638, 1991; Withers et al., *Mol Cell Biol.*, 11:4864, 1991) and ectopic expression in transgenic mice promotes hyperplasia and adenocarcinomas (Wang et al., *Nature*, 369:669, 1994).

In contrast, ectopic expression of cyc1aAt did not result in neoplasia but stimulated organized growth, without altering meristem organization or size as monitored by confocal microscopy. Moreover, morphology of the transgenic plants was not altered and increased growth was accompanied by accelerated organ development. Thus, cyclin expression is a crucial, limiting upstream factor in an intrinsic regulatory hierarchy governing meristem activity, organized growth and indeterminate plant development. This regulatory hierarchy, which is distinctly different from that in animals, where determinate development limits proliferative growth, exemplified by the strict morphogenetic control of cell division during muscle differentiation (Halevy et al., *Science*, 267:1018, 1995; Skapek et al., *Science*, 267:1022, 1995), may underlie the striking plasticity of plant growth and development (Drew, M. C., *New Phytol.*, 75:479, 1975). Cyclin abundance may function as a rheostat to allow flexible growth control in response to changes in the environment such as nutrient availability.

TABLE 1

| Plant line | | Root apical growth | | |
|---|---|---|---|---|
| | | Rate [μm.h⁻¹] | % of wild-type | n |
| Col-0 | (−) | 254.1 | 100 | 57 |
| 2A5 | (−) | 253.1 | 99.6 | 56 |
| 3A | (+) | 341.4* | 134.4 | 20 |
| 3A | (−) | 259.4 | 102.1 | 30 |
| 4A3 | (+) | 291.6* | 114.8 | 47 |
| 6A | (+) | 354.1* | 139.5 | 20 |
| 6A | (−) | 252.4 | 99.3 | 16 |
| 7A | (+) | 344.9* | 135.7 | 24 |
| 7A | (−) | 249.8 | 98.3 | 19 |
| 8A | (+) | 335.4* | 131.9 | 21 |
| 8A | (−) | 258.6 | 101.8 | 31 |
| 11A1 | (−) | 258.8 | 101.8 | 45 |
| 2A5 | (−) | 253.1 | 99.6 | 56 |

Table 1 shows a comparison of root apical growth rates. Plant line=independent transformants (except for Col-0). (+)=plants that show enhanced growth phenotype due to presence of adequate levels of cyclin-encoding nucleic acid. (−)=plants that have lost introduced cyclin-encoding nucleic acid or do not exhibit sufficient cyclin expression for enhanced growth. Rate=rate of displacement of root apex per unit time. (*denotes values significantly different from Wild-Type growth rate.) n=number of individual plants analyzed.

TABLE 2

| | Plant line | | | | | |
|---|---|---|---|---|---|---|
| | Col-0 (wild type) | | 7A (transgenic) | | 8A (transgenic) | |
| Cell Type | Size [μm] | n | Size [μm] | n | Size [μm] | n |
| Epidermis | 137 | 37 | 129 | 34 | 158 | 12 |
| Cortex | 159 | 31 | 135* | 7 | 160 | 9 |

TABLE 2-continued

| Cell Type | Col-0 (wild type) Size [μm] | n | 7A (transgenic) Size [μm] | n | 8A (transgenic) Size [μm] | n |
|---|---|---|---|---|---|---|
| Endodermis | 109 | 23 | 90* | 22 | 107 | 11 |
| Pericycle | 73 | 26 | 67 | 19 | 71 | 57 |

TABLE 3

Growth of seedling root system.

| Plant line | Fresh weight [mg] 3d | 6d | Dry weight [mg] 3d | 6d | DNA per root [μg] 3d | 6d |
|---|---|---|---|---|---|---|
| Col-0 | 11 | 25 | 1.7 | 2.4 | 5 | 14 |
| 4A3 | 31 | 136 | 4.5 | 15.4 | 8 | 35 |
| 6A | 30 | 155 | 4.2 | 19.3 | 10 | 46 |
| 7A | 24 | 156 | 3.5 | 16.8 | 9 | 38 |
| 8A | 18 | 134 | 2.5 | 12.8 | 8 | 33 |

Table 2 shows a comparison of cell size; and Table 3 shows a comparison of root growth after IAA treatment in wild-type and in transgenic Arabidopsis lines containing the cdc2aAt::cyc1aAt gene fusion. The lines 3A, 6A, 7A, 8A are heterozygous T1 populations with more than one introduced transgene; (+) denotes plants with increased cyc1aAt transcript levels, (−) plants with wild-type cyc1aAt transcript levels. The following T2 lines are homozygous for cdc2aAt::cyc1aAt::cyc1aAt: 2A5, 4A3 and 11A1; constitutive cyc1aAt expression in 4A3, but not in 2A5 and 11A1, exceeds IAA-induced wild-type levels (FIG. 1). n, number of plants analyzed. *, means that are significantly different from the wild-type; for a, $P<0.001$, for b, $P<0.01$. Fresh weight=weight of freshly excised root system. Dry weight=weight after 24 hours of drying.

The foregoing description of the invention is exemplary for purposes of illustration and explanation. It should be understood that various modifications can be made without departing from the spirit and scope of the invention.

Accordingly, the following claims are intended to be interpreted to embrace all such modifications.

What is claimed is:

1. A recombinant plant exhibiting increased root growth as compared to the corresponding wild-type plant, wherein said recombinant plant comprises a recombinant nucleic acid encoding a cyc1aAt protein operably associated with a regulatory sequence.

2. The recombinant plant of claim 1, wherein said regulatory sequence is a promoter.

3. The recombinant plant of claim 2, wherein said promoter is selected from the group consisting of constitutive promoters and inducible promoters.

4. The recombinant plant of claim 1, wherein said nucleic acid is contained within a T-DNA derived vector.

5. Recombinant plant tissue derived from the recombinant plant of claim 1.

6. A recombinant seed derived from the recombinant plant of claim 5.

7. A recombinant plant exhibiting increased root growth as compared to the corresponding wild-type plant produced by the method of:

contacting plant cells with a nucleic acid encoding a cyc1aAt protein, wherein said nucleic acid is operably associated with a regulatory sequence to obtain transformed plant cells;

producing plants from said transformed plant cells; and selecting a plant exhibiting said increased growth and yield.

8. Recombinant plant tissue derived from the recombinant plant of claim 7.

9. The recombinant seed derived from the recombinant plant of claim 8.

* * * * *

SEQUENCE LISTING

```
<160> NUMBER OF SEQ ID NOS: 2

<210> SEQ ID NO 1
<211> LENGTH: 1618
<212> TYPE: DNA
<213> ORGANISM: A. Thaliana
<220> FEATURE:
<221> NAME/KEY: CDS
<222> LOCATION: (89)...(1372)

<400> SEQUENCE: 1
catagaagac gagacgcccc cactacttag acttttctca ctacaaacct gagattttag      60
tctgagagaa agagaagaga acactaag atg atg act tct cgt tcg att gtt        112
                              Met Met Thr Ser Arg Ser Ile Val
                                1               5 cct caa caa tcc acg gat gat gtt gtt gtg gta gat ggc aaa aac gta      160
Pro Gln Gln Ser Thr Asp Asp Val Val Val Val Asp Gly Lys Asn Val
        10                  15                  20 gcg aaa gga aga aac cgt caa gtt ctt ggt gat ata ggt aat gtt gtt      208
Ala Lys Gly Arg Asn Arg Gln Val Leu Gly Asp Ile Gly Asn Val Val
 25                  30                  35                  40 cga gga aat tac cca aag aac aac gaa ccg gaa aag atc aat cat cgt      256
Arg Gly Asn Tyr Pro Lys Asn Asn Glu Pro Glu Lys Ile Asn His Arg
                 45                  50                  55 cct cgt aca cga tct caa aat ccc acg ctt ctt gtg gag gat aat ctc      304
Pro Arg Thr Arg Ser Gln Asn Pro Thr Leu Leu Val Glu Asp Asn Leu
             60                  65                  70 aaa aaa cct gta gtc aag aga aac gca gta cca aag ccg aag aaa gtg      352
```

-continued

```
                    Lys Lys Pro Val Val Lys Arg Asn Ala Val Pro Lys Pro Lys Lys Val
                             75                  80                  85 gct ggg aat cca aag gta gta gac gtg att gag ata agt tca gac agt         400
Ala Gly Asn Pro Lys Val Val Asp Val Ile Glu Ile Ser Ser Asp Ser
     90                  95                 100 gat gaa gaa ctt ggt tta gtt gct gct cga gag aag aag gct act aag         448
Asp Glu Glu Leu Gly Leu Val Ala Ala Arg Glu Lys Lys Ala Thr Lys
105                 110                 115                 120 aag aaa gcg acc act tac aca tct gtt ctt act gct aga agc aag gct         496
Lys Lys Ala Thr Thr Tyr Thr Ser Val Leu Thr Ala Arg Ser Lys Ala
                125                 130                 135 gct tgt ggt tta gag aag aaa cag aaa gaa aag att gtt gat atc gat         544
Ala Cys Gly Leu Glu Lys Lys Gln Lys Glu Lys Ile Val Asp Ile Asp
            140                 145                 150 tct gct gat gtt gag aat gac ctc gca gct gtg gaa tat gtg gaa gat         592
Ser Ala Asp Val Glu Asn Asp Leu Ala Ala Val Glu Tyr Val Glu Asp
            155                 160                 165 att tac agt ttt tac aag tct gtt gag agt gaa tgg agg cca cga gat         640
Ile Tyr Ser Phe Tyr Lys Ser Val Glu Ser Glu Trp Arg Pro Arg Asp
170                 175                 180 tac atg gca tct cag cct gat att aat gaa aag atg aga ctg atc ctg         688
Tyr Met Ala Ser Gln Pro Asp Ile Asn Glu Lys Met Arg Leu Ile Leu
185                 190                 195                 200 gtg gag tgg ttg att gat gtg cat gtc cga ttc gag cta aac ccg gaa         736
Val Glu Trp Leu Ile Asp Val His Val Arg Phe Glu Leu Asn Pro Glu
                205                 210                 215 aca ttt tac ctc act gtt aac att ctg gat cgg ttc ttg tcg gtt aag         784
Thr Phe Tyr Leu Thr Val Asn Ile Leu Asp Arg Phe Leu Ser Val Lys
            220                 225                 230 cca gtg cct cga aaa gaa ctg cag ctt gtt ggt ctc agt gct ctt ctc         832
Pro Val Pro Arg Lys Glu Leu Gln Leu Val Gly Leu Ser Ala Leu Leu
            235                 240                 245 atg tcg gcc aag tat gaa gaa att tgg cca cca cag gtg gag gat cta         880
Met Ser Ala Lys Tyr Glu Glu Ile Trp Pro Pro Gln Val Glu Asp Leu
250                 255                 260 gtt gat att gca gac cat gca tac agt cac aaa cag att ctg gtg atg         928
Val Asp Ile Ala Asp His Ala Tyr Ser His Lys Gln Ile Leu Val Met
265                 270                 275                 280 gag aag aca ata ctg tct aca ctt gag tgg tac ttg aca gtt ccg act         976
Glu Lys Thr Ile Leu Ser Thr Leu Glu Trp Tyr Leu Thr Val Pro Thr
                285                 290                 295 cat tat gtc ttc cta gct cgt ttc atc aaa gct tcc att gca gac gaa         1024
His Tyr Val Phe Leu Ala Arg Phe Ile Lys Ala Ser Ile Ala Asp Glu
            300                 305                 310 aag atg gag aat atg gtg cac tat ttg gct gag tta ggc gta atg cat         1072
Lys Met Glu Asn Met Val His Tyr Leu Ala Glu Leu Gly Val Met His
            315                 320                 325 tac gat acg atg ata atg ttc agt cca tca atg gta gct gct tct gca         1120
Tyr Asp Thr Met Ile Met Phe Ser Pro Ser Met Val Ala Ala Ser Ala
330                 335                 340 atc tac gca gca aga tct tct ctc cgc caa gtt ccc ata tgg acc agc         1168
Ile Tyr Ala Ala Arg Ser Ser Leu Arg Gln Val Pro Ile Trp Thr Ser
345                 350                 355                 360 act ctc aag cat cac act ggc tat tct gag act cag ctc atg gac tgt         1216
Thr Leu Lys His His Thr Gly Tyr Ser Glu Thr Gln Leu Met Asp Cys
                365                 370                 375 gca aag ctg ttg gcg tat cag caa tgg aag caa caa gaa gaa ggg agt         1264
Ala Lys Leu Leu Ala Tyr Gln Gln Trp Lys Gln Gln Glu Glu Gly Ser
            380                 385                 390
```

```
gag agc agt act aag gga gct tta cga aag aaa tac tcc aag gac gaa    1312
Glu Ser Ser Thr Lys Gly Ala Leu Arg Lys Lys Tyr Ser Lys Asp Glu
        395                 400                 405 cgc ttc gct gtg gct ttg atc cct ccg gcc aaa gct ttg ttg acc gga    1360
Arg Phe Ala Val Ala Leu Ile Pro Pro Ala Lys Ala Leu Leu Thr Gly
410                 415                 420 act gaa tct gct taggagttag gaccctttaa gaagacgaag aagctgaaga        1412
Thr Glu Ser Ala
425 accaagccta gtttcatttt ccttctgaaa atcaagtcta gtttcattag ataatggtat   1472 tttgaacaag tctaatgagt cgctttgaaa cctagtcctt tagcatgatt cattcccaaa   1532 cactgcatat cttgtaagaa gtcagtttct tccgagaagt ttaatttcct tagatataat   1592 attctgtggt ttaaaaaaaa aaaaaa                                       1618

<210> SEQ ID NO 2
<211> LENGTH: 428
<212> TYPE: PRT
<213> ORGANISM: A Thaliana

<400> SEQUENCE: 2

Met Met Thr Ser Arg Ser Ile Val Pro Gln Gln Ser Thr Asp Asp Val
1               5                   10                  15

Val Val Asp Gly Lys Asn Val Ala Lys Gly Arg Asn Arg Gln Val
            20                  25                  30

Leu Gly Asp Ile Gly Asn Val Val Arg Gly Asn Tyr Pro Lys Asn Asn
        35                  40                  45

Glu Pro Glu Lys Ile Asn His Arg Pro Arg Thr Arg Ser Gln Asn Pro
    50                  55                  60

Thr Leu Leu Val Glu Asp Asn Leu Lys Lys Pro Val Val Lys Arg Asn
65                  70                  75                  80

Ala Val Pro Lys Pro Lys Lys Val Ala Gly Asn Pro Lys Val Val Asp
                85                  90                  95

Val Ile Glu Ile Ser Ser Asp Ser Asp Glu Glu Leu Gly Leu Val Ala
            100                 105                 110

Ala Arg Glu Lys Lys Ala Thr Lys Lys Ala Thr Thr Tyr Thr Ser
        115                 120                 125

Val Leu Thr Ala Arg Ser Lys Ala Ala Cys Gly Leu Glu Lys Lys Gln
    130                 135                 140

Lys Glu Lys Ile Val Asp Ile Asp Ser Ala Asp Val Glu Asn Asp Leu
145                 150                 155                 160

Ala Ala Val Glu Tyr Val Glu Asp Ile Tyr Ser Phe Tyr Lys Ser Val
                165                 170                 175

Glu Ser Glu Trp Arg Pro Arg Asp Tyr Met Ala Ser Gln Pro Asp Ile
            180                 185                 190

Asn Glu Lys Met Arg Leu Ile Leu Val Glu Trp Leu Ile Asp Val His
        195                 200                 205

Val Arg Phe Glu Leu Asn Pro Glu Thr Phe Tyr Leu Thr Val Asn Ile
    210                 215                 220

Leu Asp Arg Phe Leu Ser Val Lys Pro Val Pro Arg Lys Glu Leu Gln
225                 230                 235                 240

Leu Val Gly Leu Ser Ala Leu Leu Met Ser Ala Lys Tyr Glu Glu Ile
                245                 250                 255

Trp Pro Pro Gln Val Glu Asp Leu Val Asp Ile Ala Asp His Ala Tyr
            260                 265                 270
```

-continued

```
Ser His Lys Gln Ile Leu Val Met Glu Lys Thr Ile Leu Ser Thr Leu
        275                 280                 285

Glu Trp Tyr Leu Thr Val Pro Thr His Tyr Val Phe Leu Ala Arg Phe
    290                 295                 300

Ile Lys Ala Ser Ile Ala Asp Glu Lys Met Glu Asn Met Val His Tyr
305                 310                 315                 320

Leu Ala Glu Leu Gly Val Met His Tyr Asp Thr Met Ile Met Phe Ser
            325                 330                 335

Pro Ser Met Val Ala Ala Ser Ala Ile Tyr Ala Ala Arg Ser Ser Leu
            340                 345                 350

Arg Gln Val Pro Ile Trp Thr Ser Thr Leu Lys His His Thr Gly Tyr
        355                 360                 365

Ser Glu Thr Gln Leu Met Asp Cys Ala Lys Leu Leu Ala Tyr Gln Gln
    370                 375                 380

Trp Lys Gln Gln Glu Glu Gly Ser Glu Ser Ser Thr Lys Gly Ala Leu
385                 390                 395                 400

Arg Lys Lys Tyr Ser Lys Asp Glu Arg Phe Ala Val Ala Leu Ile Pro
            405                 410                 415

Pro Ala Lys Ala Leu Leu Thr Gly Thr Glu Ser Ala
            420                 425
```